(12) United States Patent
Hoxha

(10) Patent No.: US 7,605,387 B2
(45) Date of Patent: Oct. 20, 2009

(54) RADIATION SHIELD

(76) Inventor: Taulant Hoxha, 475 Clifton Ave., Second Floor, Clifton, NJ (US) 07011

( * ) Notice: Subject to any disclaimer, the term of this patent is extended or adjusted under 35 U.S.C. 154(b) by 252 days.

(21) Appl. No.: 11/863,597

(22) Filed: Sep. 28, 2007

(65) Prior Publication Data

US 2008/0078962 A1 Apr. 3, 2008

Related U.S. Application Data

(60) Provisional application No. 60/847,469, filed on Sep. 28, 2006.

(51) Int. Cl.
*G21F 3/02* (2006.01)

(52) U.S. Cl. ............... 250/516.1; 250/515.1; 2/49.1; 378/203

(58) Field of Classification Search ........... 250/515.1, 250/516.1, 519.1; 2/16, 19, 47, 48, 49.1, 2/111, 455, 456; 378/203
See application file for complete search history.

(56) References Cited

U.S. PATENT DOCUMENTS

| 3,883,749 | A  | * | 5/1975  | Whittaker et al. | 250/516.1 |
| 4,852,141 | A  | * | 7/1989  | Horn             | 378/147   |
| 5,099,135 | A  | * | 3/1992  | Gemmill          | 250/516.1 |
| 6,325,538 | B1 | * | 12/2001 | Heesch           | 378/203   |
| 7,465,947 | B2 | * | 12/2008 | Magram           | 250/515.1 |
| 2007/0252095 | A1 | * | 11/2007 | Magram        | 250/515.1 |
| 2008/0078962 | A1 | * | 4/2008  | Hoxha          | 250/516.1 |

* cited by examiner

*Primary Examiner*—Bernard E Souw
(74) *Attorney, Agent, or Firm*—Panitch Schwarze Belisario & Nadel LLP

(57) ABSTRACT

A device for shielding at least a region of a creature from exposure to unwanted radiation during the use of an x-ray or other medical diagnostic machine or equipment includes one of a first portion sized and configured to shield an upper extremities region of the creature and a second portion sized and configured to shield a lower extremities region of the creature. The first and second portions are comprised of two opposite end regions constructed of a radiation absorbing material and connected by a middle region constructed of a non-radiation absorbing material.

18 Claims, 4 Drawing Sheets

RADIATION SHIELD

CROSS-REFERENCE TO RELATED APPLICATIONS

The present application claims the benefit of U.S. Provisional Patent Application No. 60/847,469, filed Sep. 28, 2006 and entitled "Hoxha Baby Shield", the entire subject matter of which is hereby incorporated by reference.

BACKGROUND OF THE INVENTION

The present invention generally relates to radiation shields and, more particularly, to a device or apparatus for shielding at least a region of a individual, such as a baby, or an animal from exposure to unwanted radiation during the use of an x-ray or other medical diagnostic machine or equipment.

It is well known that exposure to radiation resulting from the taking of an x-ray for medical or diagnostic purposes may be dangerous to an individual or animal and may cause cancer if the individual or animal receives and excessive dosage of x-ray radiation. The danger of x-ray radiation increases significantly in infants, younger individuals or relatively sensitive or weak individuals or animals because hospitals and other medical diagnostic centers typically do not have radiation shields designed to conform to the size and shape of these individuals or animals. Further, it is important that the patient stay relatively motionless or immobile when the x-ray is being taken or other diagnostic procedure is being preformed so that the resulting x-ray or other image will come out clear and without any rotation which may cause misdiagnosis. Obviously, keeping a baby, animal or other individual who does not desire that their x-ray be taken, immobile may be a difficult task to achieve. Therefore, it is often necessary that the parent or radiographer hold the baby, individual or animal immobile while another radiographer takes the x-ray exposure. This not only endangers the baby, animal or individual from the x-ray exposure, but also puts the parent or holding radiographer at risk for being exposed to unwanted radiation. Further, by holding the baby, animal or individual down on the examination table, the baby, animal or individual often becomes scared and agitated, which makes it difficult to take the x-ray and creates an unpleasant environment.

Therefore, it would be desirable to create a device or apparatus that is sized, configured and shaped to shield, cover or enclose certain regions of a baby, individual or animal to prevent exposure of unwanted radiation during the use of an x-ray or other medical diagnostic machine or equipment. Further, it would be desirable to create a device or apparatus that assists a parent or radiographer in maintaining the baby, individual or animal in a relatively flat and spread out configuration to assure that the baby, individual or animal is immobilized during the x-ray to avoid potential misdiagnosis. Further, it would be desirable to create a device or apparatus that eliminates the exposure of the parent and/or radiographer due to the size, configuration and weight of the device in properly restraining and immobilizing the baby, individual or animal.

BRIEF SUMMARY OF THE INVENTION

Briefly stated, the present disclosure is directed to a device for shielding regions of a baby from exposure to unwanted radiation during the use of an x-ray or other medical diagnostic machine or equipment. The device includes an upper portion sized and configured to shield an upper extremities region of the baby and a lower portion sized and configured to shield a groin region and a lower extremities region of the baby. Further, the device includes at least one attachment member removably engageable to both the upper and lower portions. The at least one attachment member removably attaches the upper portion to the lower portion at a predetermined spaced-apart distance to expose an image receptor region generally located at a chest and mid-section region of the baby when the device is placed on the baby.

In another aspect, the present disclosure is directed to a radiation shielding apparatus adapted to shield regions of an individual from exposure to unwanted radiation during the use of an x-ray or other medical diagnostic machine or equipment. The apparatus includes an upper portion sized to generally cover a portion of an upper extremities region of the individual and a lower portion sized to generally cover a portion of a lower extremities region of the individual. The apparatus further includes an attachment member that removably attaches the upper portion to the lower portion at a predetermined spaced-apart distance to expose an area generally located at a mid-section of the individual.

In yet another aspect, the present disclosure is directed to a device for shielding at least a region of a creature from exposure to unwanted radiation during the use of an x-ray or other medical diagnostic machine or equipment. The device includes one of a first portion sized and configured to shield an upper extremities region of the creature and a second portion sized and configured to shield a lower extremities region of the creature. Further, the first and second portions are comprised of two opposite end regions constructed of a radiation absorbing material and connected by a middle region constructed of a non-radiation absorbing material.

BRIEF DESCRIPTION OF THE SEVERAL VIEWS OF THE DRAWINGS

The following detailed description of a preferred embodiment of the invention will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
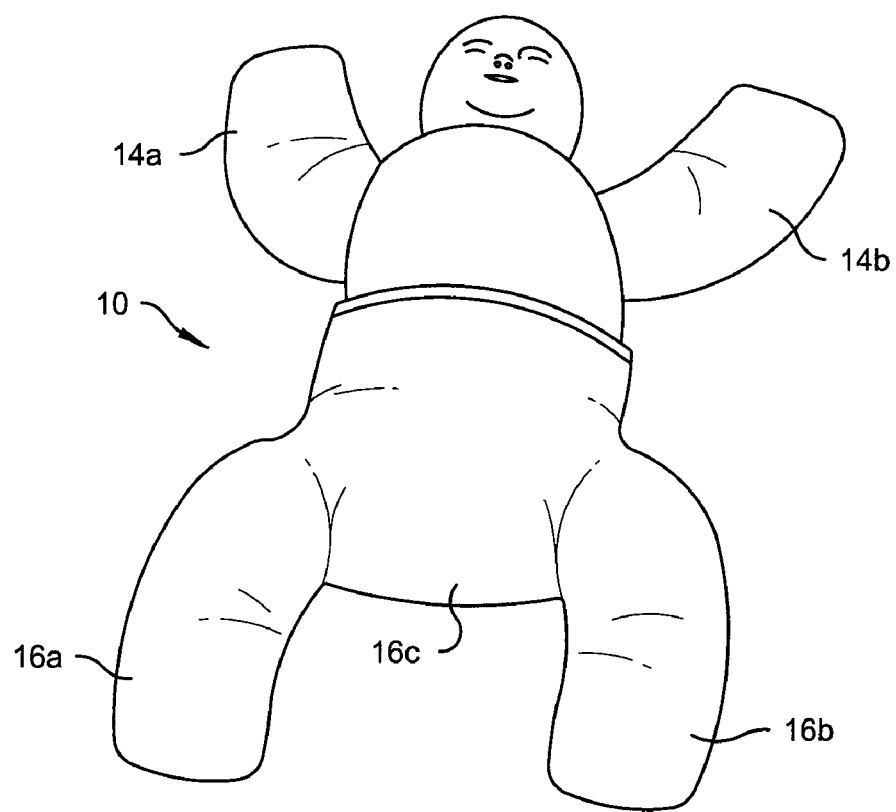
FIG. 1 is a front perspective view of a manikin in the form of an infant displaying a radiation shield in accordance with a preferred embodiment of the present invention.

Certain terminology is used in the following description for convenience only, and is not limiting. The words "right," "left," "upper," and "lower" designate directions in the drawings to which reference is made. The terminology includes the words above specifically mentioned, derivatives thereof, and words of similar import.

Referring to the drawings in detail, wherein like numerals indicate like elements throughout, there is shown in FIGS. 1-8 a preferred embodiment of a device or apparatus, generally designated 10, for shielding at least a region of a baby, animal or individual from exposure to unwanted radiation during the use of an x-ray or other medical diagnostic machine or equipment. In the preferred embodiment, the device or apparatus 10 includes a first or upper portion 14 to generally shield an upper extremities region, a second lower portion 16 to generally shield a lower extremities region and at least one attachment member 18 to removably attach the upper portion 14 to the lower portion 16. However, it is understood by those skilled in the art that the device 10 is not limited to the inclusion of the upper portion 14, the lower portion 16 and the at least one attachment member 18, but may include any combination thereof or each element independent of the others. Further, those skilled in the art would understand that the device 10 may be configured for use with creatures or individuals of various sizes and shapes without departing from the spirit in scope of the invention. For example, device 10 may be comprised of one or more integrally formed pieces to prevent exposure to unwanted radiation of at least a portion of an individual, animal or infant.

Figure 2:
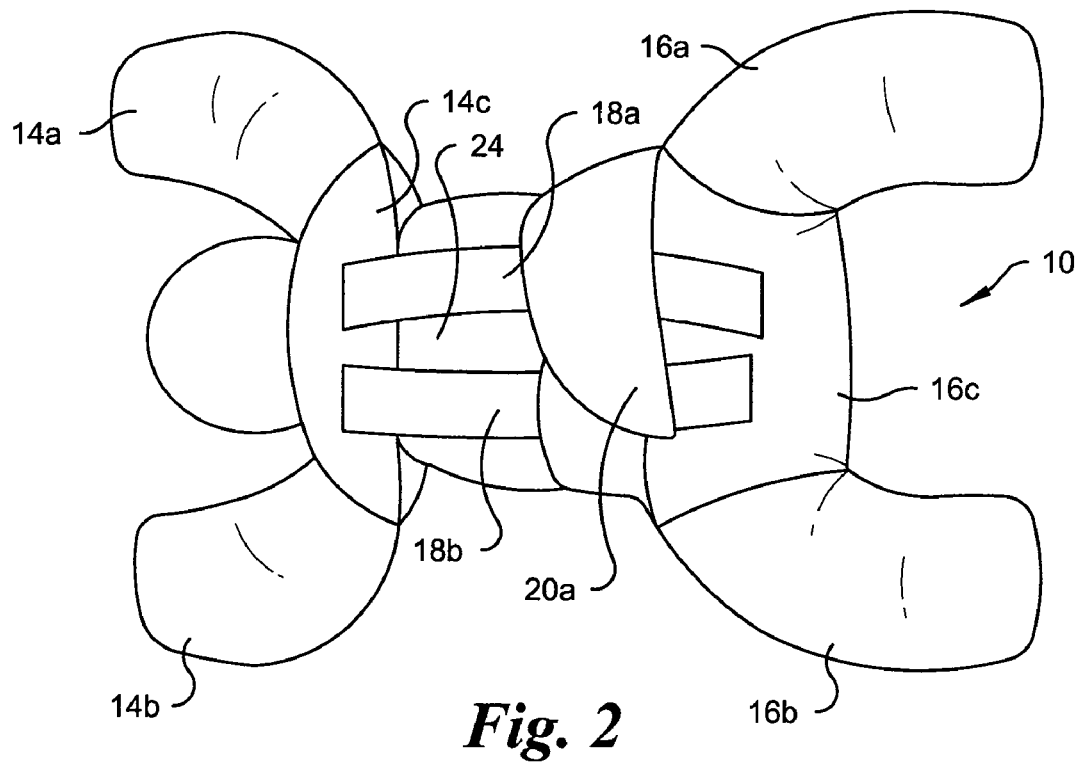
FIG. 2 is rear perspective view of the manikin displaying the radiation shield shown in FIG. 1.
Figure 3:
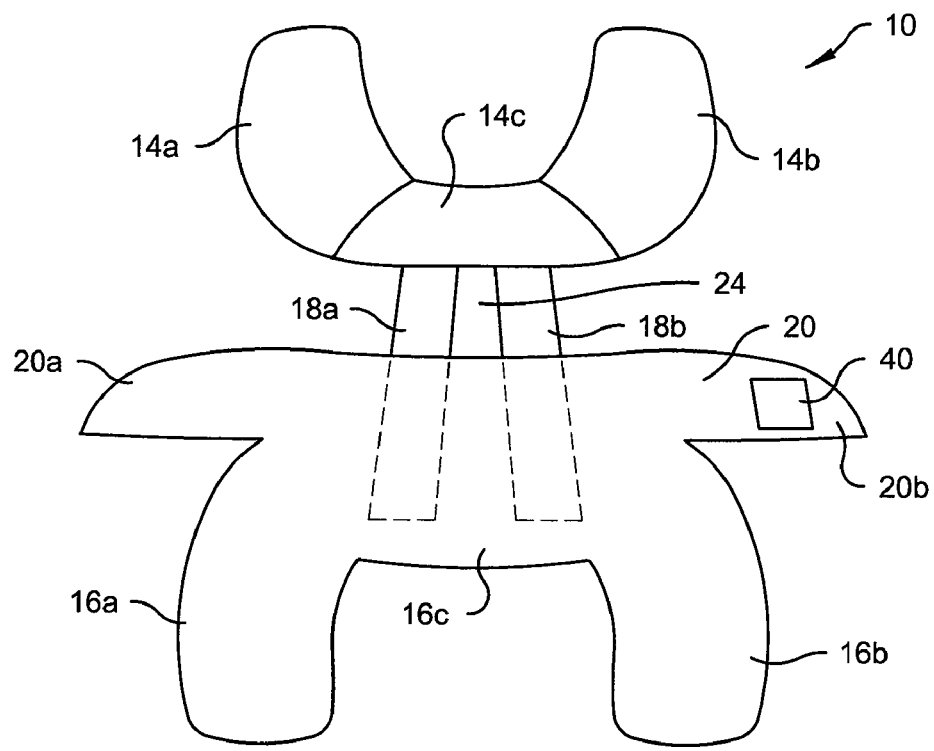
FIG. 3 is a front perspective view of the radiation shield shown in FIG. 1.
Figure 4:
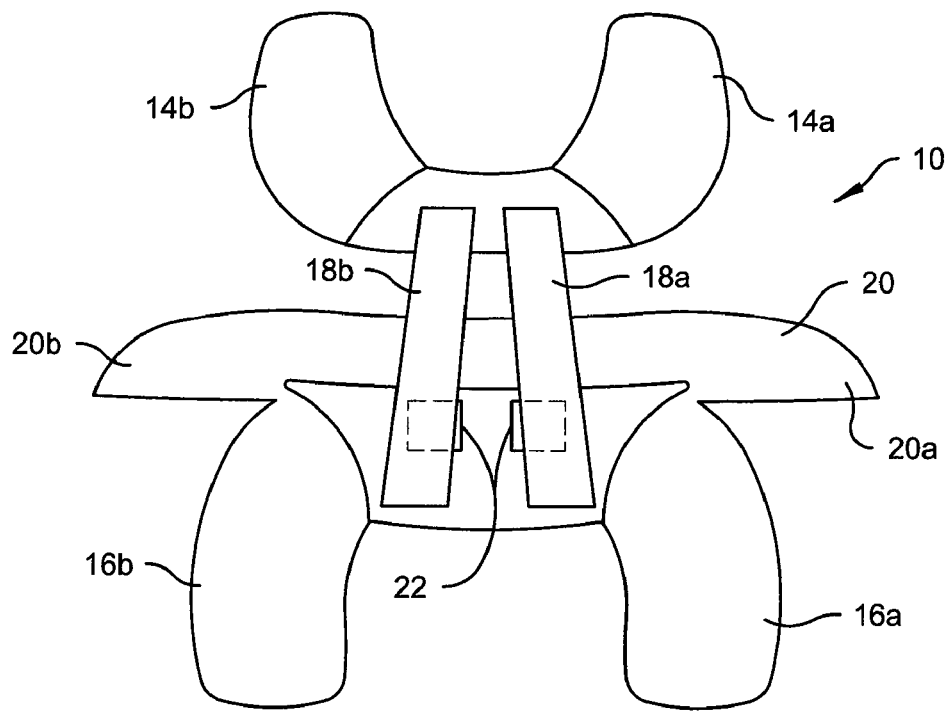
FIG. 4 is a rear perspective view of the radiation shield shown in FIG. 1.
Figure 5:
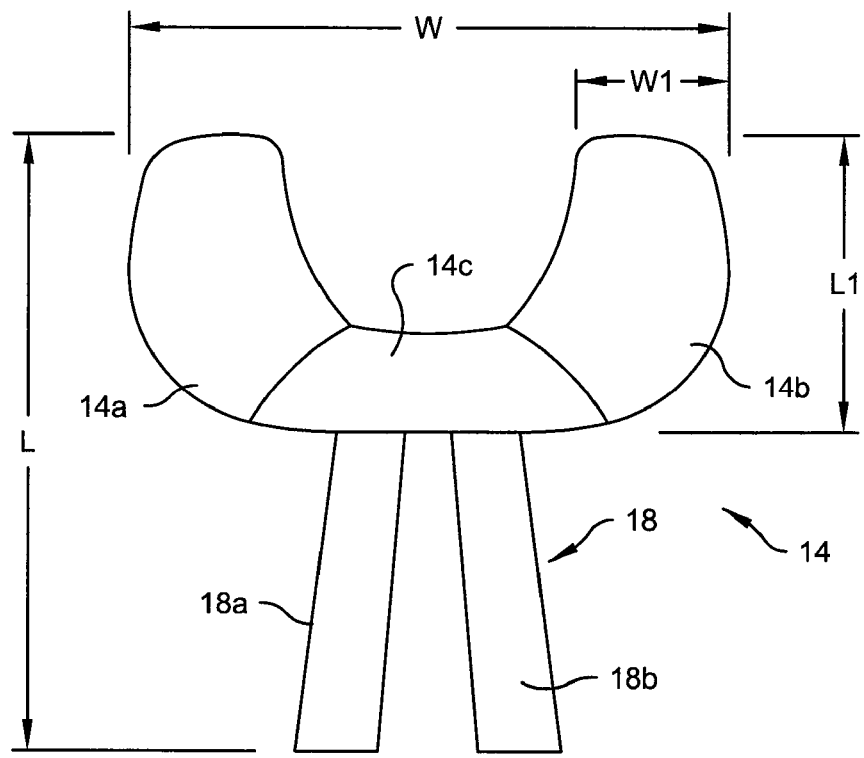
FIG. 5 is a front perspective view of a first or upper portion connected to an attachment member of the radiation shield shown in FIG. 1.
Figure 6:
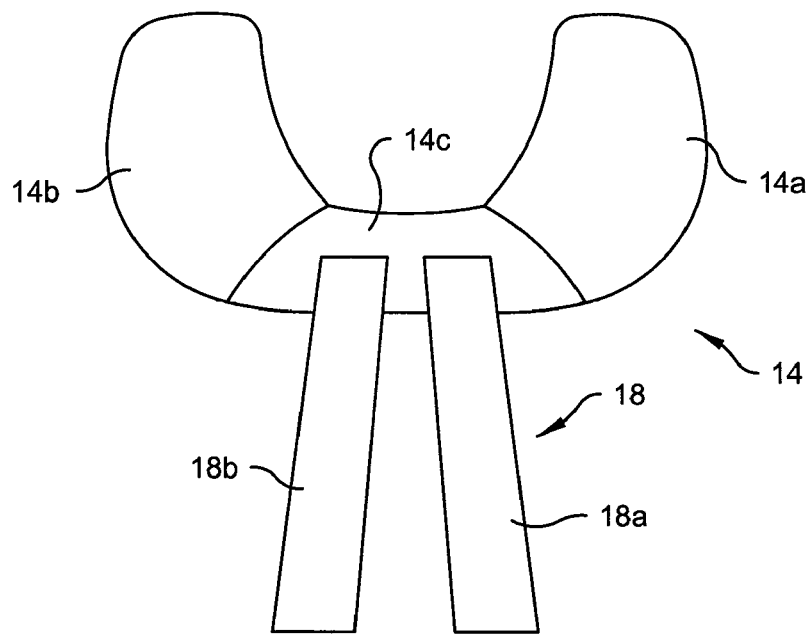
FIG. 6 is a rear perspective view of the first or upper portion connected to the attachment member of the radiation shield shown in FIG. 1.

Referring to FIGS. 1-6, the first or upper portion 14 is generally sized and configured to shield and/or cover an upper extremities region of a baby, individual or animal. Preferably, the first portion 14 is generally U-shaped when viewed from above or below and is configured to conform to an animal, baby or other individual's extended arms or upper extremities region. The first portion 14 has an overall length L preferably approximately 22 inches and a width W of preferably approximately 18 inches. However, it is understood by those skilled in the art that the first portion 14 is not limited to the size and shape described above, but may be virtually any size or shape, such as rectangular or ovular without departing from the spirit and scope of the present invention. The first portion 14 includes a front surface (as seen in FIGS. 1, 3 and 5) and a rear surface (as seen in FIGS. 2, 4 and 6). The front surface includes, but is not limited to, an aesthetically pleasing color, pattern, indicia or other similar design, while the rear surface has a plain appearance. However, it is understood by those skilled in the art that the appearance of either surface can be modified, such as to increase or decrease the aesthetic appearance or value of the device 10 without departing from the spirit and scope of the present invention. Further, the rear surface is preferably generally flush against the table top or counter top during the taking of the x-ray.

The first portion 14 includes two opposite end regions, a left end 14a and a right end 14b that are constructed of a radiation absorbing material. The opposite end regions 14a, 14b are preferably connected by a middle region 14c that is constructed of a non-radiation absorbing material. The left and right ends 14a, 14b have a length L1 preferably approximately 12 inches and a width W1 of preferably approximately 4 inches. Preferably, the opposite end regions 14a, 14b of the first portion 14 are constructed of a lead-based material, which significantly absorbs and blocks radiation. However, it is understood by those skilled in the art that the end regions 14a, 14b and middle region 14c are not limited to be constructed of a radiation absorbing material and a non-radiation absorbing material, respectively. For example, it is within the spirit and scope of the present disclosure that the two opposite end regions 14a, 14b are constructed of a non-radiation absorbing material while the middle region 14c is constructed of a radiation absorbing material. Preferably, the opposite end regions 14a, 14b of the first portion 14 are in the form of a sleeve, or glove, to completely enclose the extended arms or upper extremities region of the baby, individual or animal. However, it is understood by those skilled in the art that the opposite end regions 14a, 14b of the first portion 14 are not limited to being in the form of a sleeve and may, alternatively, be in the form of a covering sheet, such as simply a flat piece of flexible or fabric material. Alternatively, the end regions 14a, 14b may have openings at both ends to allow the baby, individual or animal's hand or paw to extend out of the far end of the sleeve.

Figure 7:
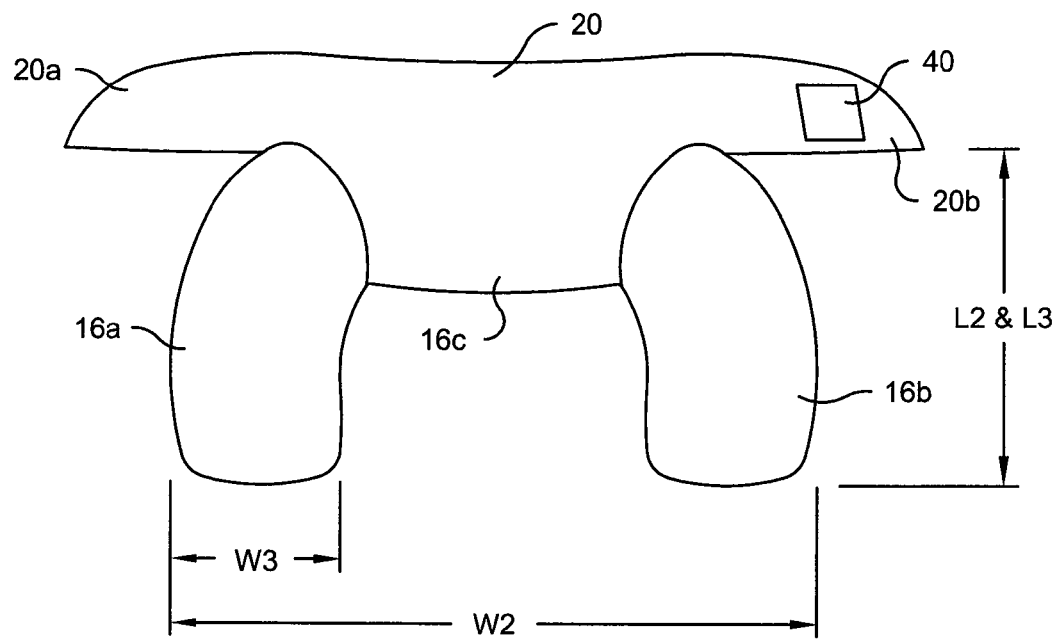
FIG. 7 is a front perspective view of a second or lower portion connected of the radiation shield shown in FIG. 1.
Figure 8:
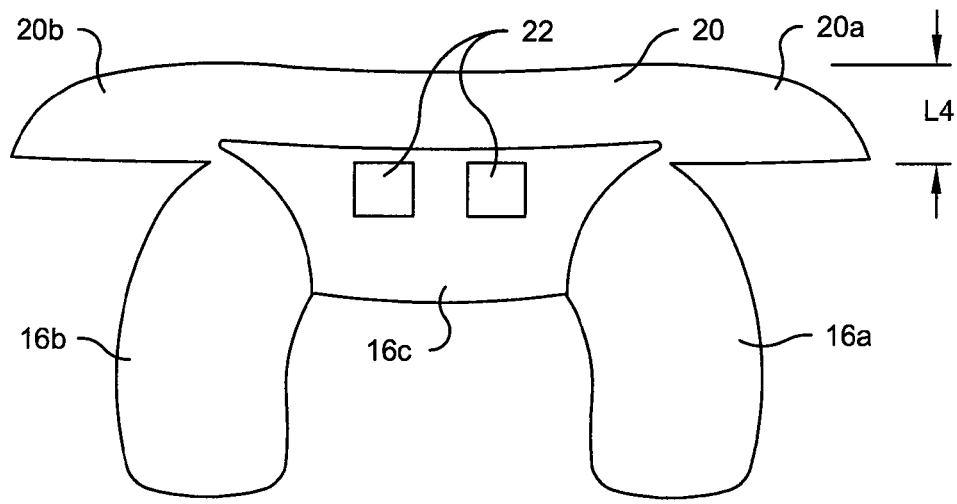
FIG. 8 is a rear perspective view of the second or lower portion of the radiation shield shown in FIG. 1.

Referring to FIGS. 1-4, 7 and 8, the second or lower portion 16 is preferably sized and configured to generally shield a groin region and a lower extremities region of the baby, individual or animal. Alternatively, the second portion 16 may be sized to only generally cover a portion of a lower extremities region of the individual, baby or animal. Preferably, the second portion 16 is generally in the shape of an inverted "U" when viewed from above or below and is configured to conform to an animal, baby or other individual's extended legs or lower extremities region. The second portion 16 has a length L2 preferably approximately 12 inches and a width W2 of preferably approximately 13 inches. However, it is understood by those skilled in the art that the second portion 16 is not limited to the size and shape described above, but may be virtually any size or shape, such as rectangular or ovular without departing from the spirit and scope of the present invention. The second portion 16 includes a front surface (as seen in FIGS. 1, 3 and 7) and a rear surface (as seen in FIGS. 2, 4 and 8). The front surface generally includes, but is not limited to, an aesthetically pleasing color, pattern, indicia or other similar design, while the rear surface has a generally plain appearance. However, it is understood by those skilled in the art that the appearance of either surface can be modified, such as to increase or decrease the aesthetic appearance or value of the device 10 without departing from the spirit and scope of the present invention. Further, the rear surface is preferably generally flush against the table top or counter top during the taking of the x-ray.

Similar to the first portion 14 of the device 10, the second portion 16 includes two opposite end regions, such as a left end region 16a and a right end region 16b, that are constructed of a radiation absorbing material. Preferably, the two opposite end regions 16a, 16b are connected by a middle region 16c constructed of a non-radiation absorbing material. The two opposite end regions 16a, 16b have a length L3 preferably approximately 12 inches and a width W3 of preferably approximately 5 inches. Preferably, the two opposite end regions 16a, 16b are constructed of a lead-based material capable of completely or significantly blocking radiation passage over an area of the baby individual or animal covered or enclosed by the second portion 16. However, it is understood by those skilled in the art that the end regions 16a, 16b and middle region 16c are not limited to be constructed of a radiation absorbing material and a non-radiation absorbing material, respectively. For example, it is within the spirit and scope of the present disclosure that the two opposite end regions 16a, 16b are constructed of a non-radiation absorbing material while the middle region 16c is constructed of a radiation absorbing material.

Preferably, the opposite end regions 16a, 16b of the second portion 16 are in the form of sleeves, or gloves, to completely enclose the legs or lower extremity region of a baby, individual or animal. However, it is understood by those skilled in the art that the opposite end regions, 16a, 16b or the second portion 16 are not limited to being in the form of a sleeve and may, alternatively, be in the form of a covering sheet, such as simply a flat piece of flexible or fabric material. Alternatively, the end regions 16a, 16b may have openings at both ends to allow the baby, individual or animal's foot or paw to extend out of the far end of the sleeve. Further, a top section of the second or lower portion 16 includes an upper, laterally extending superior border 20 capable of being folded downwardly to expose a greater area of the mid-section of the baby, individual or animal for certain x-ray exams. A portion of a lower side of the superior boarder 20 is integrally formed with a portion of the top second of the second portion 16. Specifically, opposite ends 20a, 20b of the superior border 20, that are spaced at a predetermined distance, are configured to extend around the mid-section of the baby, individual or animal and removably engage each other to secure the second portion 16 to the baby, individual or animal. Preferably, each opposite end 20a, 20b includes a tab 40 formed of hook-and-loop material. However, it is understood by those skilled in the art that virtually any attachment structure may be used, such as a hook or clip on one or both opposite ends 20a, 20b, without departing from the spirit and scope of the present invention.

As seen in FIGS. 2-4, 7 and 8, at least one attachment device 22 is preferably located on the rear surface of the second or lower portion 16. Preferably, the at least one attachment device 22 is comprised of two predetermined spaced-apart tabs of hook-end-loop material. Preferably, the superior border 20 has a length L4 of approximately 3.5 inches. However, it is understood by those skill in the art that the size and shape of the second or lower portion 16 is not limited to the specified dimensions described above and may be modified without departing from the spirit and scope of the present invention. Further, the number and form of the at least one attachment device 22 may be modified, such as being formed of two or more buttons or adhesive structures, without departing from the spirit and scope of the present invention.

Referring to FIGS. 2 and 3, the at least one attachment member 18 removably engages both the first or upper portion 14 and second or lower portion 16 at a predetermined spaced-apart distance to expose an image receptor region 24, such as a cassette or film, for example, generally located behind the baby, individual, or animal at a chest or mid-section region of the baby, individual or animal when the device 10 is placed on the baby, individual, or animal. Thus, the image receptor region 24 is located between the at least one attachment member 18 and the baby, individual or animal when the device is placed on the baby, individual, or animal. It is understood by those of ordinary skill in the art that the image receptor region 24, which captures the x-ray or other diagnostic image, may have a width of approximately 8 to 10 inches, for example, and a length of 10 to 12 inches for example. However, it is within the spirit and scope of the present invention that image receptor regions 24, such as a cassette or film, of various sizes and shapes may be used to capture the x-ray image, or other diagnostic image, when using the device 10. Further, it is understood by those of ordinary skill in the art that multiple image receptor regions 24 may be used and placed at various locations on the baby, individual, or animal in conjunction with the device 10.

The at least one attachment member 18 is comprised of at least one strip of hook-and-loop material. Preferably, the at least one attachment member 18 is comprised of two laterally spaced strips 18a, 18b of hook-and-loop material that generally extend parallel to each other to removably engage the middle regions 14c, 16c of the upper and lower portions 14, 16, respectively. However, it is understood by those skilled in the art that the form, number and orientation of the at least one attachment member 18 may be modified without departing from the spirit and scope of the present invention. For example, the two strips 18a, 18b may be configured in the shape of an "X" or may be in the form or clips, buttons or adhesive strips. Further, it is understood by those skilled in the art that the at least one attachment member 18 may be adjusted to change the predetermined distance between the first and second portions 14, 16 depending on the length or height of the baby, individual or animal.

In operation, the parent or radiographer first assembles the device 10 by attaching the first or upper portion 14 to the second or lower portion 16 by the at least one attachment member 18 before placing the device 10 on the baby, individual or animal. Next, the parent or radiographer places the first or upper portion 14 of the device 10 onto the baby, individual or animal by placing the upper extremities of the baby, individual or animal into the sleeves of the two opposite end regions 14a, 14b. Then, the second or lower portion 16 is placed onto the baby, individual or animal by placing the lower extremities of the baby, individual or animal into the sleeves of the two opposite end regions 16a, 16b such that the image receptor region 24 is generally located between the baby, individual, or animal and the at least one attachment member 18 at a portion of a mid-section region of the baby, individual or animal. The opposite ends 20a, 20b of the superior boarder 20 may now be extended and connected around the back side of the baby, individual or animal to more securely attach the device 10 to the baby, individual or animal. Alternatively, the superior boarder 20 may be folded downwardly if the parent or radiographer desires to expose a larger region of the baby, individual or animal for the x-ray.

It is understood by those skilled in the art that inherent weight of the radiation absorbing material used to construct the opposite end regions 14a, 14b, 16a, 16b of the first and second portions 14, 16, respectively, will help assist the parent or radiographer in immobilizing the baby, individual or animal during the x-ray. However, it is within the spirit and scope of the present invention that the device 10 includes additional restraining structure, such as hooks, clips or ties, on various portions of the first or second portions 14, 16 or the at least one attachment means 18 to assist the parent or radiographer in immobilizing the baby, individual or animal. Further, the inherent weight and thickness of the material used to construct the first and second portions 14, 16 may create a certain level of comfort and warmth for the baby, individual or animal in the often cold and unpleasant medical facilities.

It will be appreciated by those skilled in the art that changes could be made to the embodiment described above without departing from the broad inventive concept thereof. It is understood, therefore, that this invention is not limited to the particular embodiment disclosed, but is intended to cover modifications within the spirit and scope of the present invention as is attributed in the present disclosure.

I claim:

1. A device for shielding regions of a baby from exposure to unwanted radiation during the use of an x-ray or other medical diagnostic machine or equipment, said device comprising:

an upper portion sized and configured to shield an upper extremities region of said baby;

a lower portion sized and configured to shield a groin region and a lower extremities region of said baby; and at least one attachment member removably engagable to both said upper and lower portions;

wherein said at least one attachment member removably attaches said upper portion to said lower portion at a predetermined spaced-apart distance to expose an image receptor region generally located at a chest and mid-section region of said baby when said device is placed on said baby.

2. The device in accordance with claim 1, wherein said upper and lower portions are comprised of two opposite end regions constructed of a radiation absorbing material and connected by a middle region constructed of a non-radiation absorbing material.

3. The device in accordance with claim 2, wherein said opposite end regions of said upper and lower portions are constructed of a lead-based material.

4. The device in accordance with claim 1, wherein a top section of said lower portion includes a superior border capable of being folded downwardly to expose a greater area of said mid-section of said baby for certain x-ray exams.

5. The device in accordance with claim 4, wherein opposite ends of the superior border are configured to extend around said mid-section of said baby and removably engage each other to secure the lower portion to said baby.

6. The device in accordance with claim 1, wherein said at least one attachment member is comprised of at least one strip of hook-and-loop material.

7. The device in accordance with claim 6, wherein the at least one attachment member is comprised of two strips of hook-and-loop material that generally extend parallel to each other to removably engage a middle region of the upper and lower portions, respectively.

8. The apparatus in accordance with claim 1, wherein said upper and lower portions are comprised of a sleeve to completely enclose said upper and lower extremities region of said baby.

9. A radiation shielding apparatus adapted to shield regions of an individual from exposure to unwanted radiation during the use of an x-ray or other medical diagnostic machine or equipment, said apparatus comprising:
an upper portion sized to generally cover a portion of an upper extremities region of said individual;
a lower portion sized to generally cover a portion of a lower extremities region of said individual; and
an attachment member removably attaches said upper portion to said lower portion at a predetermined spaced-apart distance to expose an area generally located at a mid-section of said individual.

10. The apparatus in accordance with claim 9, wherein said upper and lower portions are comprised of a sleeve to completely enclose said upper and lower extremities region of said individual.

11. The device in accordance with claim 9, wherein said upper and lower portions are comprised of two opposite end regions constructed of a radiation absorbing material and connected by a middle region constructed of a non-radiation absorbing material.

12. The device in accordance with claim 9, wherein a top section of said lower portion includes a superior border capable of being folded downwardly to expose a greater area of said mid-section of said individual for certain x-ray exams.

13. The device in accordance with claim 9, wherein the attachment member is comprised of two strips of hook-and-loop material that generally extend parallel to each other to removably engage a middle region of the upper and lower portions, respectively.

14. The apparatus in accordance with claim 9, wherein said individual is selected from the group consisting of infants, children and individuals between the age of 0 to 18 months old.

15. The apparatus in accordance with claim 9, wherein said individual is selected from the group consisting of infants, children and individuals within the weight range of 0 to 50 pounds.

16. The apparatus in accordance with claim 9, wherein said individual is an animal.

17. The apparatus in accordance with claim 9, wherein said individual is mentally or physically challenged.

18. A device for shielding at least a region of a creature from exposure to unwanted radiation during the use of an x-ray or other medical diagnostic machine or equipment, said device comprising:
one of a first portion sized and configured to shield an upper extremities region of said creature and a second portion sized and configured to shield a lower extremities region of said creature;
wherein said first and second portions are comprised of two opposite end regions constructed of a radiation absorbing material and connected by a middle region constructed of a non-radiation absorbing material.

* * * * *